(12) United States Patent
Pushko et al.

(10) Patent No.: US 6,296,854 B1
(45) Date of Patent: Oct. 2, 2001

(54) LIVE ATTENUATED VENEZUELAN EQUIRE ENCEPHALITIS VACCINE

(75) Inventors: Peter Pushko; Michael D. Parker, both of Frederick; Jonathan F. Smith, Sabillasville; Bruce J. Crise, Frederick, all of MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/454,721

(22) Filed: Dec. 7, 1999

Related U.S. Application Data

(60) Provisional application No. 60/111,330, filed on Dec. 7, 1998, now abandoned.

(51) Int. Cl.$^7$ .................................................. A61K 39/12
(52) U.S. Cl. ................................. 424/218.1; 424/205.1; 424/199.1; 424/820; 435/236; 435/235
(58) Field of Search ............................... 435/235.1, 236, 435/320.1; 424/199.1, 205.1, 218.1, 820

(56) References Cited

FOREIGN PATENT DOCUMENTS

WO 98/50529  11/1998  (WO) .
WO 98/53077  11/1998  (WO) .

OTHER PUBLICATIONS

Brutlag et al., (1990) Comp. App. Biosci. 6:237–245.
Wertz, et al., "Gene rearrangement attenuates expression and lethality of a nonsegmented negative strand RNA virus" PNAS USA, vol. 95, pp. 3501–3506 (Mar. 1998).
(Medline Abstract) Becker et al., "PCR detection of amplified 132 porepeats in Marek's disease . . . ," taken from Virus Genes, 7(3), pp. 277–287 (Sep. 1993).
Pushko, et al., "Replicon–Helper Systems from Attenuated Venezuelan Equine Encephalitis Virus: Expression of Heterologous Genes in Vitro and Immunization against Heterologous Pathogens in Vivo," Virology 239, pp. 389–401 (1997).

Pushko et al., "Replicon–Helper Systems from Attenuated Venezuelan Equine Encephalitis Virus: Expression of Heterologous Genes in Vitro and Immunization against Heterologous Pathogens in Vivo", Virology 239:389–401 (1997).

Davis et al., "Attenuated Mutants of Venezuelan Equine encephalitis Virus Containing Lethal Mutations in the PE2 Cleavage Signal Combined with a Second–Site Suppressor Mutation in E1," Virology 212:102–110 (1995).

Strauss and Strauss, "The Alphaviruses: Gene Expression, Replication and Evolution", Microbiological Reviews, vol. 58, No. 3, Sep. 1994, p. 491–562.

Walton and Grayson, "Venezuelan Equine Encephalomyelitis", The Arboviruses: Epidemiology and Ecology, vol. IV, Chapter 46, pp. 203–220.

Davis et al., "In Virto Synthesis of Infectious Venezuelan Equine encephalitis Virus RNA from a cDNA Clone: Analysis of a Viable Detection Mutant", Virology 171: 189–204 (1989).

Rice et al., "Production of Infectious RNA Transcripts from Sindbis Virus cDNA Clones: Mapping of Lethal Mutations, Rescue of a Temperature–Sensitive Marker, and In Vitro Mutagenesis to Generate Defined Mutants", J. of VIrology, vol. 61, No. 12, Dec. 1987, p. 3809–3819.

Kuhn et al., "Chimeric Sindbis–Ross River Viruses To Study Interactions between Alphavirus Nonstructural and Structural Regions," J. of Virology, vol. 70, 1996, pp. 7900–7909.

*Primary Examiner*—Mary E. Mosher
(74) *Attorney, Agent, or Firm*—Elizabeth Arwine; Charles H. Harris

(57) ABSTRACT

A live attenuated Venezuelan equine encephalitis virus (VEE) is described which comprises a viral gene rearrangement. This rearranged attenuated virus is useful as vaccine for protection against infection with VEE. Methods of preparing the virus and methods of using the virus are described.

4 Claims, 1 Drawing Sheet

Generation of RVE and Sequence of pRVE1.1 Junction Sites and pRVE4.1

Bold type - sequences from E1 and 26S promoter controlling capsid expression.
Plain type - sequences joining E1 and the second 26S promoter.

SEQUENCE LISTING

<160> NUMBER OF SEQ ID NOS: 3

<210> SEQ ID NO 1
<211> LENGTH: 62
<212> TYPE: DNA
<213> ORGANISM: Venezuelan Equine Encephalitis Virus
<220> FEATURE:

<400> SEQUENCE: 1
atacagcagc aataggatgt atacgcggtt gacggaccta                40
taactctcta cggccaacct ga                                   62

<210> SEQ ID NO 2
<211> LENGTH: 354
<212> TYPE: DNA
<213> ORGANISM: Venezuelan Equine Encephalitis Virus
<220> FEATURE:
<221> NAME/KEY: n
<222> LOCATION: 125, 208
<223> OTHER INFORMATION: clone of recombinant virus of Venezuelan Equine
      Encephalitis Virus

<400> SEQUENCE: 2

```
atacagcagc aattggcaag ctgcttacat agaactcgcg              40
gcgattggca tgccgcttta aaattttat tttattttc                80 ttttctttc cgaatcggat tttgttttta atattcaagc              120
ttatngatac agcagcaatt ggcaagctgc ttagaaaaac             160
tgtaaggaaa taactgataa ggaattggac aagaaaatga             200
aggagctngc cgccgtcatg agcgaccctg acctggaaac             240
tgagactatg tgcctccacg acgacgagtc gtgtcgctac             280
gaagggcaag tcgctgttta ccaggatgta tacgcggttg             320
acggacccta taactctc tacggctaac ctga                     354
```

<210> SEQ ID NO 3
<211> LENGTH: 11459
<212> TYPE: DNA
<213> ORGANISM: Venezuelan Equine Encephalitis Virus
<220> FEATURE:

<400> SEQUENCE: 3

```
atgggcggcg catgagagaa gcccagacca attacctacc              40
caaaatggag aaagttcacg ttgacatcga ggaagacagc              80
ccattcctca gagctttgca gcggagcttc ccgcagtttg             120
aggtagaagc caagcaggtc actgataatg accatgctaa             160
tgccagagcg ttttcgcatc tggcttcaaa actgatcgaa             200
acggaggtgg acccatccga cacgatcctt gacattggaa             240
gtgcgcccgc ccgcagaatg tattctaagc acaagtatca             280
ttgtatctgt ccgatgagat gtgcggaaga tccggacaga             320
ttgtataagt atgcaactaa gctgaagaaa aactgtaagg             360
aaataactga taaggaattg gacaagaaaa tgaaggagct             400
cgccgccgtc atgagcgacc ctgacctgga aactgagact             440
atgtgcctcc acgacgacga gtcgtgtcgc tacgaagggc             480
aagtcgctgt ttaccaggat gtatacgcgg ttgacggacc             520
gacaagtctc tatcaccaag ccaataaggg agttagagtc             560
gcctactgga taggctttga caccaccct tttatgttta             600 agaacttggc tggagcatat ccatcatact ctaccaactg             640
ggccgacgaa accgtgttaa cggctcgtaa cataggccta             680
tgcagctctg acgttatgga gcggtcacgt agagggatgt             720
ccattcttag aaagaagtat ttgaaaccat ccaacaatgt             760
tctattctct gttggctcga ccatctacca cgagaagagg             800
gacttactga ggagctggca cctgccgtct gtatttcact             840
tacgtggcaa gcaaaattac acatgtcggt gtgagactat             880
agttagttgc gacgggtacg tcgttaaaag aatagctatc             920
agtccaggcc tgtatgggaa gccttcaggc tatgctgcta             960
cgatgcaccg cgagggattc ttgtgctgca aagtgacaga             1000
cacattgaac ggggagaggg tctcttttcc cgtgtgcacg             1040
```

| | |
|---|---|
| tatgtgccag ctacattgtg tgaccaaatg actggcatac | 1080 |
| tggcaacaga tgtcagtgcg gacgacgcgc aaaaactgct | 1120 |
| ggttgggctc aaccagcgta tagtcgtcaa cggtcgcacc | 1160 |
| cagagaaaca ccaataccat gaaaaattac cttttgcccg | 1200 |
| tagtggccca ggcatttgct aggtgggcaa aggaatataa | 1240 |
| ggaagatcaa gaagatgaaa ggccactagg actacgagat | 1280 |
| agacagttag tcatggggtg ttgttgggct tttagaaggc | 1320 |
| acaagataac atctatttat aagcgcccgg atacccaaac | 1360 |
| catcatcaaa gtgaacagcg atttccactc attcgtgctg | 1400 |
| cccaggatag gcagtaacac attggagatc gggctgagaa | 1440 |
| caagaatcag gaaaatgtta gaggagcaca aggagccgtc | 1480 |
| acctctcatt accgccgagg acgtacaaga agctaagtgc | 1520 |
| gcagccgatg aggctaagga ggtgcgtgaa gccgaggagt | 1560 |
| tgcgcgcagc tctaccacct ttggcagctg atgttgagga | 1600 |
| gcccactctg gaagccgatg tcgacttgat gttacaagag | 1640 |
| gctggggccg gctcagtgga gacacctcgt ggcttgataa | 1680 |
| aggttaccag ctacgctggc gaggacaaga tcggctctta | 1720 |
| cgctgtgctt tctccgcagg ctgtactcaa gagtgaaaaa | 1760 |
| ttatcttgca tccaccctct cgctgaacaa gtcatagtga | 1800 |
| taacacactc tggccgaaaa gggcgttatg ccgtggaacc | 1840 |
| ataccatggt aaagtagtgg tgccagaggg acatgcaata | 1880 |
| cccgtccagg actttcaagc tctgagtgaa agtgccacca | 1920 |
| ttgtgtacaa cgaacgtgag ttcgtaaaca ggtacctgca | 1960 |
| ccatattgcc acacatggag gagcgctgaa cactgatgaa | 2000 |
| gaatattaca aaactgtcaa gcccagcgag cacgacggcg | 2040 |
| aatacctgta cgacatcgac aggaaacagt gcgtcaagaa | 2080 |
| agaactagtc actgggctag ggctcacagg cgagctggtg | 2120 |
| gatcctccct tccatgaatt cgcctacgag agtctgagaa | 2160 |
| cacgaccagc cgctccttac caagtaccaa ccataggggt | 2200 |
| gtatggcgtg ccaggatcag gcaagtctgg catcattaaa | 2240 |
| agcgcagtca ccaaaaaaga tctagtggtg agcgccaaga | 2280 |
| aagaaaactg tgcagaaatt ataagggacg tcaagaaaat | 2320 |
| gaaagggctg gacgtcaatg ccagaactgt ggactcagtg | 2360 |
| ctcttgaatg gatgcaaaca ccccgtagag accctgtata | 2400 |
| ttgacgaagc ttttgcttgt catgcaggta ctctcagagc | 2440 |
| gctcatagcc attataagac ctaaaaaggc agtgctctgc | 2480 |
| ggggatccca aacagtgcgg tttttttaac atgatgtgcc | 2520 |
| tgaaagtgca tttaaccac gagatttgca cacaagtctt | 2560 |
| ccacaaaagc atctctcgcc gttgcactaa atctgtgact | 2600 |

```
tcggtcgtct caaccttgtt ttacgacaaa aaaatgagaa        2640
cgacgaatcc gaaagagact aagattgtga ttgacactac        2680
cggcagtacc aaacctaagc aggacgatct cattctcact        2720
tgtttcagag ggtgggtgaa gcagttgcaa atagattaca        2760
aaggcaacga aataatgacg gcagctgcct ctcaagggct        2800
gacccgtaaa ggtgtgtatg ccgttcggta caaggtgaat        2840
gaaaatcctc tgtacgcacc cacctcagaa catgtgaacg        2880
tcctactgac ccgcacggag gaccgcatcg tgtggaaaac        2920
actagccggc gacccatgga taaaaacact gactgccaag        2960
taccctggga atttcactgc cacgatagag gagtggcaag        3000
cagagcatga tgccatcatg aggcacatct tggagagacc        3040
ggaccctacc gacgtcttcc agaataaggc aaacgtgtgt        3080
tgggccaagg ctttagtgcc ggtgctgaag accgctggca        3120
tagacatgac cactgaacaa tggaacactg tggattattt        3160
tgaaacggac aaagctcact cagcagagat agtattgaac        3200
caactatgcg tgaggttctt tggactcgat ctggactccg        3240
gtctattttc tgcacccact gttccgttat ccattaggaa        3280
taatcactgg gataactccc cgtcgcctaa catgtacggg        3320
ctgaataaag aagtggtccg tcagctctct cgcaggtacc        3360
cacaactgcc tcgggcagtt gccactggaa gagtctatga        3400
catgaacact ggtacactgc gcaattatga tccgcgcata        3440
aacctagtac ctgtaaacag aagactgcct catgctttag        3480
tcctccacca taatgaacac ccacagagtg acttttcttc        3520
attcgtcagc aaattgaagg gcagaactgt cctggtggtc        3560
ggggaaaagt tgtccgtccc aggcaaaatg gttgactggt        3600
tgtcagaccg gcctgaggct accttcagag ctcggctgga        3640
tttaggcatc ccaggtgatg tgcccaaata tgacataata        3680
tttgttaatg tgaggacccc atataaatac catcactatc        3720
agcagtgtga agaccatgcc attaagctta gcatgttgac        3760
caagaaagct tgtctgcatc tgaatcccgg cggaacctgt        3800
gtcagcatag gttatggtta cgctgacagg gccagcgaaa        3840
gcatcattgg tgctatagcg cggcagttca agttttcccg        3880
ggtatgcaaa ccgaaatcct cacttgaaga gacggaagtt        3920
ctgtttgtat tcattgggta cgatcgcaag gcccgtacgc        3960
acaatcctta caagctttca tcaaccttga ccaacattta        4000
tacaggttcc agactccacg aagccggatg tgcaccctca        4040
tatcatgtgg tgcgagggga tattgccacg gccaccgaag        4080
gagtgattat aaatgctgct aacagcaaag gacaacctgg        4120 cggagggtgtg tgcggagcgc tgtataagaa gttcccggaa        4160
agcttcgatt tacagccgat cgaagtagga aaagcgcgac        4200
```

-continued

```
tggtcaaagg tgcagctaaa catatcattc atgccgtagg         4240
accaaacttc aacaaagttt cggaggttga aggtgacaaa         4280
cagttggcag aggcttatga gtccatcgct aagattgtca         4320
acgataacaa ttacaagtca gtagcgattc cactgttgtc         4360
caccggcatc ttttccggaa acaaagatcg actaacccaa         4400
tcattgaacc atttgctgac agctttagac accactgatg         4440
cagatgtagc catatactgc agggacaaga aatgggaaat         4480
gactctcaag gaagcagtgg ctaggagaga agcagtggag         4520
gagatatgca tatccgacga ctcttcagtg acagaacctg         4560
atgcagagct ggtgagggtg catccgaaga gttctttggc         4600
tggaaggaag ggctacagca caagcgatgg caaaactttc         4640
tcatatttgg aagggaccaa gtttcaccag gcggccaagg         4680
atatagcaga aattaatgcc atgtggcccg ttgcaacgga         4720
ggccaatgag caggtatgca tgtatatcct cggagaaagc         4760
atgagcagta ttaggtcgaa atgccccgtc gaagagtcgg         4800
aagcctccac accacctagc acgctgcctt gcttgtgcat         4840
ccatgccatg actccagaaa gagtacagcg cctaaaagcc         4880
tcacgtccag aacaaattac tgtgtgctca tcctttccat         4920
tgccgaagta tagaatcact ggtgtgcaga agatccaatg         4960
ctcccagcct atattgttct caccgaaagt gcctgcgtat         5000
attcatccaa ggaagtatct cgtggaaaca ccaccggtag         5040
acgagactcc ggagccatcg gcagagaacc aatccacaga         5080
ggggacacct gaacaaccac cacttataac cgaggatgag         5120
accaggacta gaacgcctga gccgatcatc atcgaagagg         5160
aagaagagga tagcataagt ttgctgtcag atggcccgac         5200
ccaccaggtg ctgcaagtcg aggcagacat tcacgggccg         5240
ccctctctat ctagctcatc ctggtccatt cctcatgcat         5280
ccgactttga tgtggacagt ttatccatac ttgacaccct         5320
ggagggagct agcgtgacca gcggggcaac gtcagccgag         5360
actaactctt acttcgcaaa gagtatggag tttctggcgc         5400
gaccggtgcc tgcgcctcga acagtattca ggaaccctcc         5440
acatcccgct ccgcgcacaa gaacaccgtc acttgcaccc         5480
agcagggcct gctcgagaac cagcctagtt ccacccccgc         5520
caggcgtgaa tagggtgatc actagagagg agctcgaggc         5560
gcttaccccg tcacgcactc ctagcaggtc ggtctcgaga         5600
accagcctgg tctccaaccc gccaggcgta aatagggtga         5640
ttacaagaga ggagtttgag gcgttcgtag cacaacaaca         5680
atgacggttt gatgcgggtg catacatctt ttcctccgac         5720
accggtcaag ggcatttaca acaaaaatca gtaaggcaaa         5760
```

-continued

| | |
|---|---|
| cggtgctatc cgaagtggtg ttggagagga ccgaattgga | 5800 |
| gatttcgtat gccccgcgcc tcgaccaaga aaagaagaa | 5840 |
| ttactacgca agaaattaca gttaaatccc acacctgcta | 5880 |
| acagaagcag ataccagtcc aggaaggtgg agaacatgaa | 5920 |
| agccataaca gctagacgta ttctgcaagg cctagggcat | 5960 |
| tatttgaagg cagaaggaaa agtggagtgc taccgaaccc | 6000 |
| tgcatcctgt tcctttgtat tcatctagtg tgaaccgtgc | 6040 |
| cttctcaagc cccaaggtcg cagtggaagc ctgtaacgcc | 6080 |
| atgttgaaag agaactttcc gactgtggct tcttactgta | 6120 |
| ttattccaga gtacgatgcc tatttggaca tggttgacgg | 6160 |
| agcttcatgc tgcttagaca ctgccagttt ttgccctgca | 6200 |
| aagctgcgca gctttccaaa gaaacactcc tatttggaac | 6240 |
| ccacaatacg atcggcagtg ccttcagcga tccagaacac | 6280 |
| gctccagaac gtcctggcag ctgccacaaa aagaaattgc | 6320 |
| aatgtcacgc aaatgagaga attgcccgta ttggattcgg | 6360 |
| cggcctttaa tgtggaatgc ttcaagaaat atgcgtgtaa | 6400 |
| taatgaatat tggaaaacgt ttaaagaaaa ccccatcagg | 6440 |
| cttactgaag aaaacgtggt aaattacatt accaaattaa | 6480 |
| aaggaccaaa agctgctgct cttttttgcga agacacataa | 6520 |
| tttcaatatg ttgcaggaca taccaatgga caggtttgta | 6560 |
| atggacttaa agagagacgt gaaagtgact ccaggaacaa | 6600 |
| aacatactga agaacggccc aaggtacagg tgatccaggc | 6640 |
| tgccgatccg ctagcaacag cgtatctgtg cggaatccac | 6680 |
| cgagagctgg ttaggagatt aaatgcggtc ctgcttccga | 6720 |
| acattcatac actgtttgat atgtcggctg aagactttga | 6760 |
| cgctattata gccgagcact tccagcctgg ggattgtgtt | 6800 |
| ctggaaactg acatcgcgtc gtttgataaa agtgaggacg | 6840 |
| acgccatggc tctgaccgcg ttaatgattc tggaagactt | 6880 |
| aggtgtggac gcagagctgt tgacgctgat tgaggcggct | 6920 |
| ttcggcgaaa tttcatcaat acatttgccc actaaaacta | 6960 |
| aatttaaatt cggagccatg atgaaatctg gaatgttcct | 7000 |
| ccacactgtt gtgaacacag tcattaacat tgtaatcgca | 7040 |
| agcagagtgt tgagagaacg gctaaccgga tcaccatgtg | 7080 |
| cagcattcat tggagatgac aatatcgtga aaggagtcaa | 7120 |
| atcggacaaa ttaatggcag acaggtgcgc cacctggttg | 7160 |
| aatatggaag tcaagattat agatgctgtg gtgggcgaga | 7200 |
| aagcgcccta tttctgtgga gggtttattt tgtgtgactc | 7240 |
| cgtgaccggc acagcgtgcc gtgtggcaga ccccctaaaa | 7280 |
| aggctgttta agcttggcaa acctctggca gcagacgatg | 7320 |
| aacatgatga tgacaggaga agggcattgc atgaagagtc | 7360 |

```
aacacgctgg aaccgagtgg gtattctttc agagctgtgc            7400
aaggcagtag aatcaaggta tgaaaccgta ggaacttcca            7440
tcatagttat ggccatgact actctagcta gcagtgttaa            7480
atcattcagc tacctgagag gggcccctat aactctctac            7520
ggctaacctg aatggactac gacatagtct agtccgccaa            7560
gatgttcccg ttccagccaa tgtatccgat gcagccaatg            7600
ccctatcgca acccgttcgc ggccccgcgc aggccctggt            7640
tccccagaac cgaccctttt ctggcgatgc aggtgcagga            7680
attaacccgc tcgatggcta acctgacgtt caagcaaagc            7720
cgggacgcgc cacctgaggg gccatccgct aagaaaccga            7760
agaaggaggc ctcgcaaaaa cagaaagggg gaggccaagg            7800
gaagaagaag aagaaccaag ggaagaagaa ggctaagaca            7840
gggccgccta tccgaaggc acagaatgga acaagaaga              7880
agaccaacaa gaaaccaggc aagagacagc gcatggtcat            7920
gaaattggaa tctgacaaga cgttcccaat catgttggaa            7960
gggaagataa acggctacgc ttgtgtggtc ggagggaagt            8000
tattcaggcc gatgcatgtg gaaggcaaga tcgacaacga            8040
cgttctggcc gcgcttaaga cgaagaaagc atccaaatac            8080
gatcttgagt atgcagatgt gccacagaac atgcgggccg            8120
atacattcaa atacacccat gagaaacccc aaggctatta            8160
cagctggcat catggagcag tccaatatga aaatgggcgt            8200
ttcacggtgc cgaaaggagt tggggccaag ggagacagcg            8240
gacgacccat tctggataac cagggacggg tggtcgctat            8280
tgtgctggga ggtgtgaatg aaggatctag gacagccctt            8320
tcagtcgtca tgtggaacga gaagggagtt accgtgaagt            8360
atactccgga gaactgcgag caatggtcac tagtgaccac            8400
catgtgtctg ctcgccaatg tgacgttccc atgtgctcaa            8440
ccaccaattt gctacgacag aaaaccagca gagactttgg            8480
ccatgctcag cgttaacgtt gacaacccgg gctacgatga            8520
gctgctggaa gcagctgtta agtgcccccgg aaggaaaagg           8560
agatccaccg aggagctgtt taaggagtat aagctaacgc            8600
gcccttacat ggccagatgc atcagatgtg cagttgggag            8640
ctgccatagt ccaatagcaa tcgaggcagt aaagagcgac            8680
gggcacgacg gttatgttag acttcagact cctcgcagt             8720
atggcctgga ttcctccggc aacttaaagg gcaggaccat            8760
gcggtatgac atgcacggga ccattaaaga gataccacta            8800
catcaagtgt cactccatac atctcgcccg tgtcacattg            8840
tggatgggca cggttatttc ctgcttgcca ggtgcccggc            8880
aggggactcc atcaccatgg aatttaagaa agattccgtc            8920
```

-continued

| | |
|---|---|
| acacactcct gctcggtgcc gtatgaagtg aaatttaatc | 8960 |
| ctgtaggcag agaactctat actcatcccc cagaacacgg | 9000 |
| agtagagcaa gcgtgccaag tctacgcaca tgatgcacag | 9040 |
| aacagaggag cttatgtcga gatgcacctc ccaggctcag | 9080 |
| aagtggacag cagtttggtt tccttgagcg gcagttcagt | 9120 |
| caccgtgaca cctcctgttg ggactagcgc cctggtggaa | 9160 |
| tgcgagtgtg gcggcacaaa gatctccgag accatcaaca | 9200 |
| agacaaaaca gttcagccag tgcacaaaga aggagcagtg | 9240 |
| cagagcatat cggctgcaga acgataagtg ggtgtatatt | 9280 |
| tctgacaaac tgcccaaagc agcgggagcc accttaaaag | 9320 |
| gaaaactgca tgtcccattc ttgctggcag acggcaaatg | 9360 |
| caccgtgcct ctagcaccag aacctatgat aaccttcggt | 9400 |
| ttcagatcag tgtcactgaa actgcaccct aagaatccca | 9440 |
| catatctaac cacccgccaa cttgctgatg agcctcacta | 9480 |
| cacgcatgag ctcatatctg aaccagctgt taggaatttt | 9520 |
| accgtcaccg gaaaagggtg ggagtttgta tggggaaacc | 9560 |
| acccgccgaa aaggttttgg gcacaggaaa cagcacccgg | 9600 |
| aaatccacat gggctaccgc acgaggtgat aactcattat | 9640 |
| taccacagat accctatgtc caccatcctg ggtttgtcaa | 9680 |
| tttgtgccgc cattgcaacc gtttccgttg cagcgtctac | 9720 |
| ctggctgttt tgcagatcta gagttgcgtg cctaactcct | 9760 |
| taccggctaa cacctaacgc taggatacca ttttgtctgg | 9800 |
| ctgtgctttg ctgcgcccgc actgcccggg ccgagaccac | 9840 |
| ctgggagtcc ttggatcacc tatggaacaa taaccaacag | 9880 |
| atgttctgga ttcaattgct gatccctctg ccgccttga | 9920 |
| tcgtagtgac tcgcctgctc aggtgcgtgt gctgtgtcgt | 9960 |
| gccttttta gtcatggccg gcgccgcagg cgccggcgcc | 10000 |
| tacgagcacg cgaccacgat gccgagccaa gcgggaatct | 10040 |
| cgtataacac tatagtcaac agagcaggct acgcaccact | 10080 |
| ccctatcagc ataacaccaa caaacatcaa gctgatacct | 10120 |
| acagtgaact tggagtacgt cacctgccac tacaaaacag | 10160 |
| gaatggattc accagccatc aaatgctgcg gatctcagga | 10200 |
| atgcactcca acttacaggc ctgatgaaca gtgcaaagtc | 10240 |
| ttcacagggg tttacccgtt catgtggggt ggtgcatatt | 10280 |
| gcttttgcga cactgagaac acccaagtca gcaaggccta | 10320 |
| cgtaatgaaa tctgacgact gccttgcgga tcatgctgaa | 10360 |
| gcatataaag cgcacacagc ctcagtgcag gcgttcctca | 10400 |
| acatcacagt gggagaacac tctattgtga ctaccgtgta | 10440 |
| tgtgaatgga gaaactcctg tgaatttcaa tggggtcaaa | 10480 |
| ttaactgcag gtccgctttc cacagcttgg acacccttg | 10520 |

```
                                                       -continued atcgcaaaat cgtgcagtat gccggggaga tctataatta              10560
tgattttcct gagtatgggg caggacaacc aggagcattt              10600
ggagatatac aatccagaac agtctcaagc tcagatctgt              10640
atgccaatac caacctagtg ctgcagagac ccaaagcagg              10680
agcgatccac gtgccataca ctcaggcacc ttcgggtttt              10720
gagcaatgga agaaagataa agctccatca ttgaaattta              10760
ccgccccttt cggatgcgaa atatatacaa accccattcg              10800
cgccaaaaac tgtgctgtag ggtcaattcc attagccttt              10840
gacattcccg acgccttgtt caccagggtg tcagaaacac              10880
cgacactttc agcggccgaa tgcactctta acgagtgcgt              10920
gtattcttcc gactttggtg ggatcgccac ggtcaagtac              10960
tcggccagca agtcaggcaa gtgcgcagtc catgtgccat              11000
cagggactgc taccctaaaa gaagcagcag tcgagctaac              11040
cgagcaaggg tcggcgacta tccatttctc gaccgcaaat              11080
atccacccgg agttcaggct ccaaatatgc acatcatatg              11120
ttacgtgcaa aggtgattgt cacccccga aagaccatat               11160 tgtgacacac cctcagtatc acgcccaaac atttacagcc              11200
gcggtgtcaa aaaccgcgtg gacgtggtta acatccctgc              11240
tgggaggatc agccgtaatt attataattg gcttggtgct              11280
ggctactatt gtggccatgt acgtgctgac caaccagaaa              11320
cataattgaa tacagcagca attggcaagc tgcttacata              11360
gaactcgcgg cgattggcat gccgctttaa aatttttatt              11400
ttatttttct tttcttttcc gaatcggatt ttgtttttaa              11440
tatttcaaaa aaaaaaaaa                                     11459
```

LIVE ATTENUATED VENEZUELAN EQUIRE ENCEPHALITIS VACCINE

This application claims benefit of provisional application serial No. 60/111,330, filed Dec. 7, 1998, now abandoned.

Venezuelan equine encephalitis virus (VEE) is a member of the alphavirus genus of the family Togaviridae which is comprised of a large group of mosquito-borne RNA viruses found throughout much of the world. The viruses normally circulate among rodent or avian hosts through the feeding activities of a variety of mosquitoes. Epizootics occur largely as a result of increased mosquito activity after periods of increased rainfall.

VEE virus has six serological subtypes (I–VI). Two of these subtypes, I and III have multiple variants. Existing vaccines for VEE are derived from VEE IA/B and have been shown to be effective in preventing disease from VEE IA/B infection. The current vaccines of VEE do not adequately protect against the VEE IE variant, as disease has occurred in laboratory workers vaccinated with a vaccine derived from VEE IA/B. Also, recent unprecedented outbreaks of VEE IE in populations of horses in Mexico indicate a need for a VEE IE vaccine.

The alphavirus vaccines currently in use throughout the United States and Canada for veterinary purposes and for human use and use by at-risk laboratory personnel are formalin-inactivated preparations. These inactivated vaccines are poorly immunogenic, require multiple inoculations and frequent boosters and are inadequately protective in the case of an aerosol exposure to the virus.

In order to develop an improved vaccine of higher immunogenicity requiring less frequent immunizations, and protective against aerosol exposure to the virus, effort has been concentrated on the development of a live-attenuated alphavirus vaccine.

The construction of full-length alphavirus clones has proven to be useful in the development of live-attenuated alphavirus vaccines. The current approach to making live-attenuated alphavirus vaccines from a DNA clone of the virus involves 1) construction of a full-length, virulent clone, 2) identification and introduction of an appropriately attenuating mutation, 3) analysis of stability of the attenuated virus with regard to the specific attenuating mutation(s) in a viable virus vaccine candidate. Points 2 and 3 often involve much effort and expense on the part of the individuals and laboratories and it is possible that the altered antigen structures resulting from the attenuating and/or suppressor mutations would render the vaccine unprotective against infection with the native virus.

Therefore, there is a need for an alphavirus vaccine which is attenuated and retains the natural antigenic structures of the native virus.

SUMMARY OF THE INVENTION

The present invention satisfies the need mentioned above.

In this application is described a live attenuated vaccine for VEE which comprises a viral gene rearrangement as a method of viral attenuation. Alphaviruses with rearranged genes are believed to encode and express native proteins without any known mutation altering the protein conformation. Therefore, the immune reaction is raised against native antigens present on the infecting virus. The gene rearrangement process also obviates the need to search for attenuating mutations and to analyze the stability of the attenuating and/or suppressor mutations.

The mutations in most live-attenuated virus vaccines often result in significantly reduced yields during production, and inadequate replication in vivo because the altered gene products are less efficient in directing virus assembly. That is not the case for the live-attenuated virus of the present invention since it replicates to titers which are equivalent to those seen with wild type, fully virulent VEE viruses.

In addition, the attenuated phenotype is likely very stable since at least two independently unlikely recombination events would by required to revert to a wild type sequence.

Animal studies demonstrated complete protection with a very low dose ($10^3$ plaque forming units, pfu) of the candidate vaccine. This is at least one order of magnitude less than the dose used for the current vaccine TC-83 and V3526 (Davis, N. L. et al., 1995, *Virology* 212, 102–110). Lower vaccination doses provide significant advantages in GMP production and potentially increase the safety of the vaccine.

The vaccine preparations of the present invention comprise the cDNA genome of VEE which has been altered such that the order of genes in the viral genome has been reversed. The resulting virus is attenuated and useful as a live vaccine for human and veterinary use.

The genome of VEE virus is a single-stranded, plus-sense RNA approximately 11,400 nucleotides in length. The 5' two-thirds of the genome consist of a non-coding region of approximately 48 nucleotides followed by a single open reading frame of approximately 7,500 nucleotides which encode the viral replicase/transcriptase. The 3' one-third of the genome encodes the viral structural proteins in the order C-E3-E2-6K-E1, each of which are derived by proteolytic cleavage of the product of a single open reading frame of approximately 3700 nucleotides. The sequences encoding the structural proteins are transcribed as a 26S mRNA from an internal promoter on the negative sense complement of the viral genome. The nucleocapsid (C) protein possesses autoproteolytic activity which cleaves the C protein from the precursor protein soon after the ribosome transits the junction between the C and E3 protein coding sequence. Subsequently, the envelope glycoproteins E2 and E1 are derived by proteolytic cleavage in association with intracellular membranes and form heterodimers. E2 initially appears in the infected cell as a precursor, pE2, which consists of E3 and E2. After extensive glycosylation and transit through the endoplasmic reticulum and the golgi apparatus, E3 is cleaved from E2 by furin-like protease activity at a cleavage site consisting of RKRR with the cleavage occuring after the last arginine residue. Subsequently, the E2/E1 complex is transported to the cell surface where it is incorporated into virus budding from the plasma membrane (Strauss and Strauss, 1994, *Microbiological Rev* 58, 491–562).

Alphavirus gene expression is biphasic in nature. The viral genome, delivered to the cell after viral and cell membrane fusion, is translated directly starting at a translational start codon located near the 5' end of the genome. The initial translation products are termed nonstructural proteins because they are not incorporated into the virion particle. These nonstructural proteins serve as polymerases that function both in transcription of viral structural genes and replication of both the positive and negative sense viral genomes. An internal promoter, i.e. 26S promoter, on the full-length negative sense viral RNA is recognized by the viral polymerase leading to transcription of the structural genes.

In a wild type alphavirus infection, there is only one structural gene transcript which gives rise to one polyprotein consisting of all the viral structural proteins. The order of the proteins encoded by the structural gene transcript is capsid protein followed by membrane glycoproteins. Upon translation, the autocatalytic activity of capsid cleaves the capsid protein from the growing nascent chain. This proteolytic event allows proper membrane translocation of the glycoproteins. The capsid proteins complex with the positive sense viral genome to form a ribonucleocapsid. It is the concerted action of the ribonucleocapsid and the glycoproteins that leads to assembly of an infectious virus particle at the plasma membrane.

Systems that employ defective alphaviral genomes lacking all structural genes can be complemented by coexpression of the structural proteins to yield infectious viral particles. Complementation can be accomplished by expression of the capsid and membrane glycoproteins from a single transcript similar to that found in a wild type viral infection. Alternatively, complementation can be carried out using two different transcripts, one encoding a self-cleaving capsid protein and a second encoding the membrane glycoprotein transcript with a translational start. Most often, the complementing genes are under control of the 26S promoter and these cassettes are flanked by the 5' and 3' untranslated termini of the virus.

Our understanding that the alphaviral structural genes could be supplied on two separate transcripts to complement a defective alphaviral genome suggested that rearrangement of the alphaviral structural genes may be employed to make a replicating alphavirus. In order to test this hypothesis, a defective alphavirus genome of VEE IA/B lacking the capsid gene, but encoding the membrane glycoprotein genes under control of the 26S promoter (VEE-REP-GP, see Examples below), was complemented by a VEE capsid gene from VEE IA/B under control of the 26S promoter and flanked by the untranslated 5' and 3' termini of the virus (capsid helper). Upon transfection of baby hamster kidney (BHK) cells with RNAs encoding VEE-REP-GP and the capsid helper, a recombinant virus was generated. Molecular analysis of the virus indicated that the structural gene order had been reversed and the glycoproteins preceeded the capsid. This virus was designated RVE (FIG. 1). Subsequent passage of RVE led to high titer stocks similar to the parental biological isolate of VEE.

Since the structural genes used to generate RVE were originally derived from a virulent clone of VEE, it was expected that RVE would be virulent. In contrast to our expectations, all animals inoculated with $10^3$, $10^5$, or $10^7$ pfu of RVE survived infection with RVE and showed no signs of disease regardless of the dose (Table 1). To test the nature of RVE as a vaccine, the inoculated animals were challenged with a dose of virulent virus sufficient to kill all unvaccinated mice. Sera collected from mice three weeks after the primary inoculation and three weeks after challenge indicated that RVE elicited a robust immune response that was not significantly increased after challenge, indicating efficient immunity had been achieved (Tables 2 and 3).

Efforts to characterize and clone the recombinant virus has led to construction of two different molecular clones designated pRVE1.1 and pRVE4.1 (FIG. 1). Subsequent sequence analysis of RVE1.1 indicated that 63 nucleotides were located between the translational stop of the E1 glycoprotein and the start of the 26S promoter controlling capsid designated intervening sequence 1.1 (SEQ ID NO:1). pRVE4.1 contained 354 nucleotides between the E1 gene and the 26S promoter designated intervening sequence 4.1 (SEQ ID NO:2). Propagation of virus derived from either pRVE1.1 or pRVE4.1 led to the generation of high titer stocks of virus of $7\times10^7$ and $2\times10^7$ pfu/ml, respectively. These titers are similar to the titers obtained from the parental biological isolate from which RVE was derived.

Studies have shown that point mutations within the nonstructural protein encoding region can cause attenuation of otherwise virulent alphaviruses. To eliminate the possibility that pRVE1.1 and pRVE4.1 contained such mutations, the entire nonstructural gene regions of both pRVE$^{1.1}$ and pRVE4.1 were replaced with sequences from a clone homologous to a virulent clone (V3526, a VEE clone isogenic with V3000). The two new clones were designated pRVE1.1.1 and pRVE4.1.4, respectively. Virus derived from pRVE1.1.1 and pRVE4.1.4 (RVE1.1.1 and RVE4.1.4) grew to titers of $2.3\times10^8$ and $1.5\times10^8$ pfu/ml, respectively. Mice were inoculated with $10^3$, $10^5$, or $10^7$ pfu per mouse. These viruses were well tolerated, with all but one mouse surviving the inoculation, whereas mice inoculated with $10^4$ pfu of wild type VEE all died. These results indicate that the virus was attenuated, and that the attenuation was the result of Capsid/structural proteins rearrangement (Table 4).

Therefore, in one aspect of the invention, the invention pertains to a DNA fragment comprising cDNA coding for an infectious VEE virus containing a gene rearrangement wherein the capsid gene is 3' to, or downstream from, the membrane glycoproteins in contrast to the wild type VEE wherein the capsid gene is 5' from, or upstream from, the membrane glycoproteins. Also provided is the RNA produced from transcription of the cDNA and the virus particles produced from the RNA in a host cell. The cDNA, RNA produced from transcription of the cDNA, and the virus particles produced from the RNA are useful as vaccines. The VEE virus encompassed are all different subtypes of VEE such as VEE I, VEE II, VEE IIIA, VEE I A/B, VEE IC, VEE ID, and VEE IE and others as described in Walton, T. E., Grayson, M. A. *Venezuelan Equine Encephalitis Virus*, In: Monath, T. P. (ed.) *The Arboviruses: Epidemiology and Ecology*, Vol IV, Boca Raton, Fla. CRC Press, 1988, p. 203–231.

In another aspect of the invention is provided a cDNA coding for a rearranged VEE virus as described above, including at least one attenuating mutation therein, the RNA produced from transcription of the cDNA and the virus particles produced from the RNA in a host cell for use as a vaccine. In another aspect of the invention the additional attenuating mutation is a cleavage deletion at the furin cleavage site of VEE.

In yet another aspect of the invention is provided a recombinant vector comprising a DNA fragment described above and a vector.

In a further aspect of the invention is provided a chimaeric virus containing nonstructural sequences from othe alphaviruses and structural sequences from VEE in a rearranged form such that the capsid gene is 3' to the structural glycoproteins to be used as a means of attenuating virulent alphaviruses.

In another aspect, the nonstructural sequences of the VEE rearranged virus can be substituted with an antigen of interest in a method and composition for expressing antigens of other alphaviruses or foreign antigens for use as potential vaccines for human and veterinary use.

In a further aspect of the invention, there is provided a vaccine protective against VEE, the vaccine comprising live attenuated VEE virus with a rearrangement as described above in an amount effective to elicit a protective immune response in an animal to VEE and a pharmaceutically acceptable diluent, carrier, or excipient. In another aspect of the invention, the vaccine comprises a VEE I A/B rearranged virus vaccine protective against protective against infection with VEE I A/B and cross protective against infection with other VEE subtypes, such as VEE IC, VEE IB, VEE IC, VEE IE and others.

In another aspect of the invention, there is provided a multivalent vaccine protective against VEE comprising one or more VEE virus strains each containing a rearragement of the structural genes such that the capsid gene is 3' to, or downstream from, the glycoproteins, the vaccine comprising rearranged, live-attenuated VEE virus in an amount effective to elicit a protective immune response in an animal to VEE and a pharmaceutically acceptable diluent.

In yet another aspect of the invention is provided a method for attenuating VEE, said method comprising gene rearrangement, wherein the capsid gene is rearranged such that it is found 3' to the structural glycoprotein in the rearranged VEE. Rearrangement can be achieved by several methods known in the art such as recombination, or artificial synthesis to name a few.

BRIEF DESCRIPTION OF THE DRAWINGS

These and other features, aspects, and advantages of the present invention will become better understood with reference to the following description and appended claims, and accompanying drawings where:

DETAILED DESCRIPTION

Figure 1:
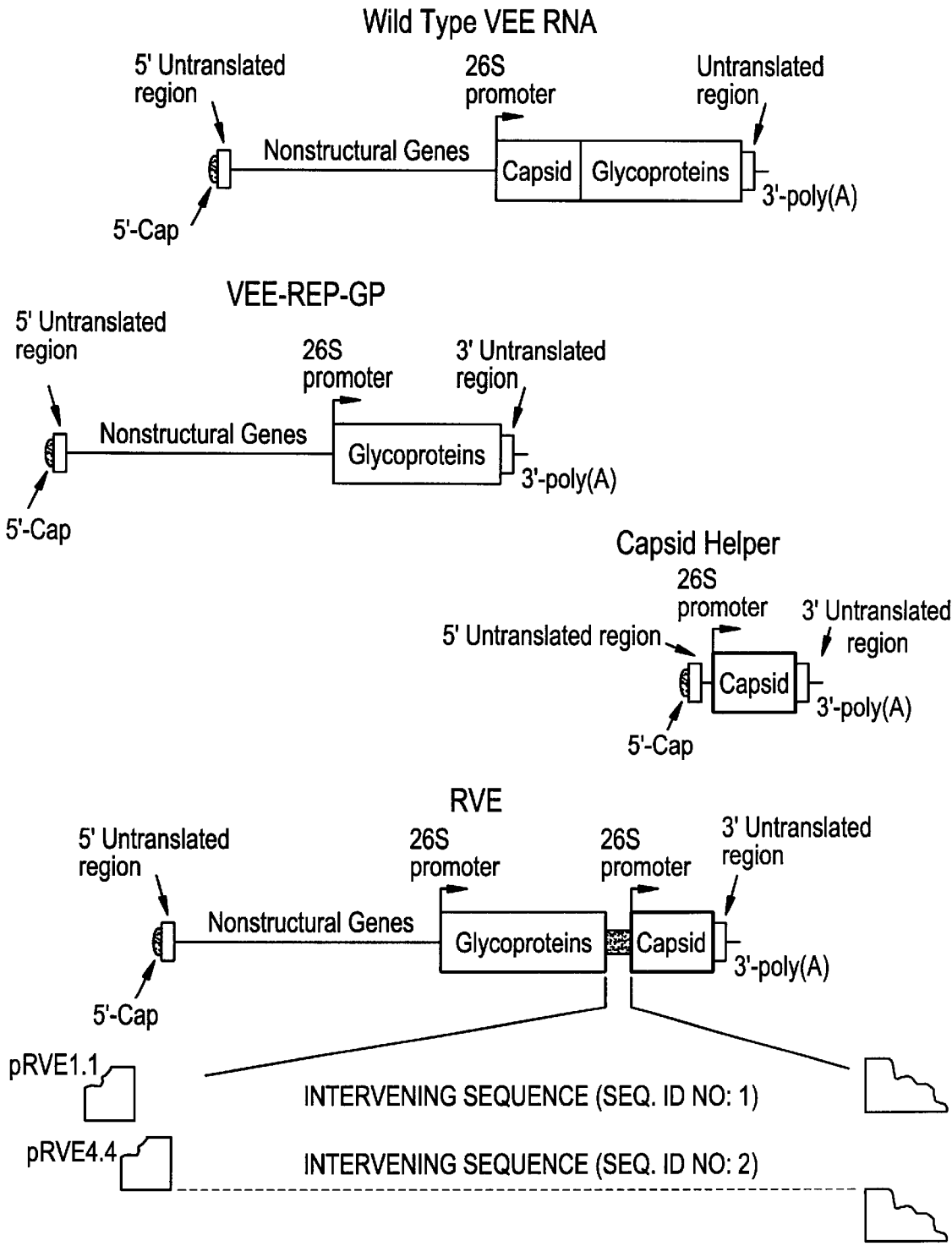
FIG. 1. Generation of RVE and sequence of molecular clones pRVE1.1 and pRVE4.1 junction sites.

In the description that follows, a number of terms used in recombinant DNA technology are extensively utilized. In order to provide a clearer and consistent understanding of the specification and claims, including the scope to be given such terms, the following definitions are provided.

In one embodiment the present invention relates to a DNA fragment comprising cDNA encoding an infectious VEE virus containing a gene rearrangement wherein the capsid gene is 3' of the structural proteins. By "gene rearrangement" is meant a change in the location of the gene from wild-type virus. In the wild-type or native VEE, the capsid gene is located 5' (with respect to the virion RNA sequence) or upstream from, or precedes the genes for the structural proteins. The rearranged VEE of the present invention has the capsid gene 3' (with respect to the virion RNA sequence), or following the structural proteins. It is preferable that a 26S promoter be located directly upstream of the capsid sequence. The promoter can be derived from any alphavirus however, some may not be recognized as well as a VEE promoter.

The present rearranged VEE was a product of a recombination between a defective alphavirus genome lacking the capsid gene, and a capsid helper containing the capsid gene under control of the 26S promoter flanked by untranslated termini of VEE. By "defective alphavirus" is meant an infectious clone of alphavirus which is able to undergo replication in the host cell, but is not encapsulated and does not produce virus particles due to the absence of the capsid protein. By "capsid helper" is meant a RNA having the 5' and 3' termini of the viral genome, a 26S promoter, and the capsid gene. The defective alphavirus and the capsid helper in the instant invention recombined, i.e. exchanged sequences at certain regions of the RNA which are similar in both the alphavirus RNA and the helper RNA, and produced an infectious VEE virus, able to replicate and form virus particles, but which was rearranged such that the capsid gene is 3' to the structural genes. This VEE virus was found to be attenuated. In accordance with standard terminology in the art, by "attenuated virus" is meant a virus with decreased probability of causing disease in its host or a virus with loss of virulence. The attenuated virus of the present invention produced a protective immune reaction in mice after inoculation, and protected mice against infection after challenge.

VEE, strain V3000 (which cDNA sequence is presented in SEQ ID NO:3), a molecular clone of the Trinidad donkey strain of VEE (I A/B) was used as a parent strain in the instant invention. Any other VEE strain which consistently kills 100% of 5 week old C57/B16 mice when inoculated subcutaneously can be used, such as 71–180, 68U201, Mucambo, to name a few. Recombinant, rearranged virus can be selected by plaque assays in cell cultures and attenuation determined through assays in mice or other animal models. The virus produced can be isolated and biologically cloned in plaque assays in Vero or baby hamster kidney (BHK) cell cultures. Such cells are known and available from ATCC for example. The viral RNA can be reverse transcribed to produce a cDNA encoding the recombinant virus as described in Davis et al., 1989, *Virology* 171, 189–204.

To determine the attenuation of the rearranged virus, mice can be inoculated subcutaneously with about $10^4$ plaque forming units of the recombinant virus. The term about provides flexibility of from ±2% to 5% of the amount indicated. The recombinant virus is considered virulent if all mice die, and not fully virulent if mice do not all die. The $LD_{50}$ of wild type VEE is 1–2 pfu, therefore, if inoculation of 10,000-fold did not cause lethal disease in all mice, it is considered attenuated. The attenuated rearranged virus can be sequenced by known methods (Davis et al., 1989, supra).

Rearranged virus of the present invention include any VEE virus which has a gene rearrangement resulting in the capsid gene downstream from the membrane glycoprotein genes of the virus in addition to other permissive rearrangements including, but not limited to, intervening sequences between the structural glycoproteins and the capsid gene ranging between about 15 nucleotides to about 1000 nucleotides wherein 'about' means a flexibility of 5% higher or lower, preferably about 25 to about 800 nucleotides, most preferably about 40 to about 400 nucleotides. The intervening sequences can be random sequences which do not interfere with the function of the coded genes, preferably viral non-coding sequences. Additional mutations to the rearranged genome can be included to increase safety or attenuation of the virus or include additional beneficial aspects to the genome, such as a foreign antigen to increase antigenicity or to provide a multivalent vaccine. By "attenuating mutation" is meant a nucleotide mutation or amino acid coded for in view of such a mutation which result in a decreased probability of causing disease in its host (i.e., a loss of virulence), in accordance with standard terminology in the art. The phrase "attenuating mutation" excludes mutations which would be lethal to the virus. The attenuating mutation may be a substitution mutation, an insertion mutation, or an in-frame deletion mutation. Attenuating mutations in the VEE may be a deletion of the four amino acids of the furin-like cleavage site between the E3 and E2 proteins.

Attenuating mutations may be introduced into cDNAs encoding live VEE by any suitable means, such as site-directed mutagenesis (see, e.g., *Current Protocols in Molecular Biology* Ausubel, F. M. et al. (Eds.) John Wiley & Sons, Inc.).

The immunogenic protein or peptide, or "immunogen" may be any immunogen suitable for protecting the subject against a disease, including but not limited to microbial, bacterial, protozoal, parasitic, and viral diseases. Preferably, the immunogen of interest is inserted along with its own 26S promoter sequence and therefore can be inserted anywhere in the rearranged virus RNA.

The sequence of the wild type VEE virus is known (SEQ ID NO:3). However, in addition to the rearranged position of the capsid protein with respect to the structural glycoprotein, the two rearranged VEE viruses related to the present invention include intervening sequences, i.e., the sequence at the site of rearrangement between the E1 glycoprotein and the 26S promoter of the capsid gene for RVE 1.1.1 and RVE4.1.4 are specified in SEQ ID NO: 1 and SEQ ID NO:2, respectively.

Isolated nucleic acid molecules of the invention include DNA molecules which comprise a sequence substantially different from those described above but which, due to the degeneracy of the genetic code, still encode the rearranged virus.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, the corresponding RNA sequence of ribonucleotides (A, G, C and U), where each thymidine deoxyribonucleotide (T) in the specified deoxyribonucleotide sequence is replace by the ribonucleotide uridine (U).

Nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

DNA or polynucleotide sequences to which the invention also relates include sequences of at least about 6 nucleotides, preferably at least about 8 nucleotides, more preferably at least about 10–12 nucleotides, most preferably at least about 15–20 nucleotides, corresponding, i.e. homologous to or complementary to, a region of rearranged VEE sequence. Preferably, the sequence of the region from which the polynucleotide is derived is homologous to or complementary to a sequence which is unique to the virus. Whether or not a sequence is unique to the virus can be determined by techniques known to those of skill in the art. For example, the sequence can be compared to sequences in databanks, e.g., GenBank. Regions from which typical DNA sequences may be derived include but are not limited to, for example, regions encoding specific epitopes, as well as non-translated regions.

The present invention further relates to variants of the nucleic acid molecules of the present invention, which encode analogs or derivatives of the rearranged VEE viruses. Variants may occur naturally, such as a natural allelic variant. By an "allelic variant" is intended one of several alternate forms of a gene occupying a given locus in the genome. Non-naturally occuring variants may be produced using art-known mutagenesis techniques.

Such variants include those produced by nucleotide substitutions, deletions, or additions. The substitutions, deletions or additions may involve one or more nucleotides. These variants may be altered in coding regions, non-coding regions or both. Alterations in the coding region may produce conservative or non-conservative amino acid substitutions, deletions or additions. Especially preferred among these are silent substitutions, additions and deletions, which do not alter the properties and activities of the rearranged VEE virus. Also especially preferred in this regard are conservative substitutions.

The present application is further directed to nucleic acid molecules at least 90%, 95%, 96%, 97%, 98% or 99% identical to a nucleic acid sequence of the rearranged virus. The above nucleic acid sequences are included irrespective of whether they encode a live VEE virus. This is because even where a particular nucleic acid molecule does not encode a live VEE virus, one of skill in the art would still know how to use the nucleic acid molecules, for instance, as a hybridization probe in order to isolate an allelic variant, or to detect virus in a sample, or in a method for designing chimeric viruses.

Due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequences of the rearranged VEE virus will encode a live virus.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding rearranged VEE. In other words, to obtain a polynucleotide having a nucleotide sequence at least 95% identical to a reference nucleotide sequence, up to 5% (5 of 100) of the nucleotides in the reference sequence may be deleted, inserted, or substituted with another nucleotide. The query sentence may be an entire sequence of the rearranged virus, or the ORF (open reading frame), or any fragment specified as described herein. The percent identity of a sequence with a reference sequence can be determined conventionally using known computer programs, for example, FASTDB computer program based on the algorithm of Brutlag et al. See Brutlag et al. (1990) *Comp. App. Biosci.* 6:237–245.

In another embodiment, the present invention relates to vectors which include the isolated DNA molecules of the present invention, host cells which are genetically engineered with the recombinant vectors.

The recombinant virus can be cloned in a suitable vector or any plasmid which contains suitable restriction endonuclease cleavage sites for cloning, an origin of replication so that the plasmid can be propagated in a bacterial host, and a selectable marker gene to maintain the plasmid in the bacterial cell during growth. The DNA sequence preferably has a complementary DNA sequence bonded thereto so that the double-stranded sequence will serve as an active template for RNA polymerase when the vector is a transcription vector. Hence the transcription vector preferably comprises a plasmid such as, for example, pBluescript KS+, pUC19, TotoX (Rice, C. M., et al. 1987, *J. Virology* 61, 3809–3819). When the DNA sequence comprises a plasmid, it is preferred that a unique restriction site be provided 3' (with respect to the virion RNA sequence) to, or down-stream from, the cDNA clone. This provides a means for linearizing the DNA sequence to enhance the efficiency of transcription of genome-length RNA in vitro.

For producing RNA transcripts of the rearranged virus, the cDNA is preferably operatively associated with a promoter region such that the promoter causes the cDNA to be transcribed in the presence of an RNA polymerase which binds to the promoter. The promoter is positioned on the 5' end (with respect to the virion RNA sequence), or upstream from, the cDNA clone. An excessive number of nucleotides between the promoter sequence and the cDNA clone will result in the inoperability of the construct. Hence, the number of nucleotides between the promoter sequence and the cDNA clone is preferably not more than eight, more preferably not more than than 5, still more preferably not more than 3, and most preferably not more than 1. Exemplary promoters useful in the present invention include, but are not limited to, T3 promoters, T7 promoters, and SP6 promoters. It is preferable that the 5' end of the in vitro transcript not have any additional nucleotides preceding the first nucleotide of the viral sequence. At the 3' end, additional nucleotides can be tolerated in the in vitro transcript but are probably lost when the virus replicates.

Transfection of cells with the RNA transcript coded by the full length genomic cDNA can be achieved by any suitable means, such as, for example, by treating the cells with DEAE dextra, treating the cells with "LIPOFECTIN", and by electroporesis. Togavirus-permissive cells, alphavirus-permissive cells, and VEE-permissive cells are cells which, upon transfection with the viral RNA transcript, are capable of producing viral particles. Alphaviruses have a broad host range. Examples of such cells include, but are not limited to, Vero cells, baby hamster kidney cells, and chicken embryo fibroblast cells, Chinese hamster ovary cells, mouse L cells, MRC-5 cells, mosquito cells such as C6-36 cells, to name a few.

More specifically, vectors exemplified include pRVE1.1, pRVE4.4, pRVE1.1.1, and pRVE4.1.4, described in Examples below.

In another embodiment of the present invention is provided a chimaeric virus containing nonstructural sequences from one alphavirus and structural sequences from other alphaviruses which could be used as a means of attenuating virulent alphaviruses. By "Structural sequences" as used herein is meant sequences encoding proteins which are required for encapsidation (e.g., packaging) of the viral genome, and include the capsid protein, E1 glycoprotein, and E2 glycoprotein. By "nonstructural sequences" is meant nonstructural protein sequences, or sequences which encode viral RNA polymerase(s) proteins. Viruses from which nonstructural sequences can be used in the chimaeric virus using VEE rearranged structural genes as the backbone clone can include for example, all strains of WEE, EEE, and Sindbis, Aura, Barmah Forest, Bebaru Cabassou, Chikungunya, Everglades, Fort Morgan, Getah, Highlands J, Kyzylagach, Mayaro, Middelburg, Mucambo, Ndumu, O'nyong-nyong, Pixuna, Ross River, Sagiyama, Semliki Forest, SAAR87, Tonate, Una, Venezuelan Equine Encephalitis, Whataroa, to name a few. Construction of the chimeric virus is done by excision of the nonstructural protein genes of the backbone virus and replacement with the desired nonstructural protein genes from another virus. This can be accomplished in one of several ways. For example, site-directed mutagenesis can be used to excise the structual protein genes and leave a restriction endonuclease digestion site at the point of deletion. The nonstructural protein genes of another alphavirus would then be cloned into that restriction site. Any virus obtained after transfection of cells with RNA transcribed from that clone would by definition be a chimeric virus.

In the case where the first and second viruses are closely related, another method can be used wherein cloned structural cDNA sequences of a second alphavirus can be digested at restriction enzyme sites which both viruses have in common. The cDNA fragments of the second virus can then be cloned into the homologous sites in the first virus nonstructural protein locus such that the resulting nonstructural protein genes of the chimeric are a composite of both. Other methods for producing a chimaeric virus are known to people in the art (Kuhn et al. [1996] *J. Virology* 70:7900–7909).

In another embodiment, the attenuated virus of the present of invention can be used in a replicon expression system. A replicon expression system consists of multiple components, preferably two or three. The first is a replicon which consists of a full length infectious clone from which all of the viral structural proteins have been deleted. A multiple cloning site can be cloned into the site previously occupied by the structural protein genes. Virtually any heterologous gene may be cloned into this cloning site. Transcription of RNA from the replicon yields an RNA capable of initiating infection of the cell identically to that seen with the full-length infectious virus clone. However, in lieu of the viral structural proteins, the heterologous antigen is expressed. The heterologous gene product is then detected by the host immune system and an appropriate immune response is then mounted. This system does not yield any progeny virus particles because there are no viral structural proteins available to package the RNA into particles.

Particles which appear structurally identical to virus particles can be produced by supplying structural proteins for packaging of the replicon RNA in trans. One helper consists of a full length rearranged VEE infectious clone from which the nonstructural protein genes are deleted. The helper retains the rearranged glycoprotein genes, the promoter for subgenomic mRNA transcription, and the viral capsid genes followed by the terminal nucleotide sequences. The helper RNA is transcribed in vitro and co-transfected with replicon RNA. Because the replicon RNA retains the sequences for packaging by the nucleocapsid protein, and because the helper lack these sequences, only the replicon RNA is packaged by the viral structural proteins and released from the cell. The particles can then be inoculated into animals similar to parent virus. The replicon particles will initiate only a single round of replication because the helpers are absent, they produce no progeny virus particles, and express only the viral nonstructural proteins and the product of the heterologous gene cloned in place of the structural proteins.

The rearranged VEE replicon can be used to express heterologous genes of interest in cells as well as a means for expressing antigens or immunogenic proteins and peptides of interest. The immunogenic protein or peptide, or "immunogen" may be any immunogen suitable for protecting the subject against a disease, including but not limited to microbial, bacterial, protozoal, parasitic, and viral diseases. For example, the immunogen can be any heterologous gene of interest, including influenza hemagglutinin, lassa fever nucleocapsid and glycoproteins, portions of bacterial toxin genes, HIV glycoprotein, Ebola glycoprotein, to name a few.

In yet another embodiment, the present invention provides inactivated virus vaccines produced from live attenuated virus preparations, either as rearranged virus with mutations as has been described for VEE or chimeric virus described above. The inactivation of live virus is well known in the art and can be for example by the use of formalin. Inactivated attenuated virus vaccine has a greater safety margin both as a final vaccine in case of incomplete inactivation,and during the manufacturing process allowing production under lower biocontainment levels.

Subjects which may be administered the live attenuated or inactivated attenuated viruses and vaccine formulations disclosed herein include human, animal, and insect (e.g. equine, donkey, pigs, rodents, hamster, monkey, poultry, birds, bovines, mosquitoes) subjects.

Vaccine formulations of the present invention comprise an immunogenic amount of a live or inactivated attenuated virus as disclosed herein in combination with a pharmaceutically acceptable carrier. An "immunogenic amount" is an amount of the attenuated virus sufficient to evoke an immune response, particularly an immune response to the protein or peptide encoded by the heterologous RNA carried by the virus, in the subject to which the virus is administered. An amount of from about $10^1$ to $10^5$ plaque forming units of the live virus per dose is suitable, depending upon the age and species of the subject being treated. Exemplary pharmaceutically acceptable carriers include, but are not limited to, sterile pyrogen-free water and sterile pyrogen-free physiological saline solution.

Administration of the live attenuated viruses disclosed herein may be carried out by any suitable means, including both parenteral injection (such as intraperitoneal, subcutaneous, or intramuscular injection), by in ovo injection in birds, and by topical application of the virus (typically carried in the pharmaceutical formulation) to an airway surface. Topical application of the virus to an airway surface can be carried out by intranasal administration (e.g. by use of dropper, swab, or inhaler which deposits a pharmaceutical formulation intranasally). Topical application of the virus to an airway surface can also be carried out by inhalation administration, such as by creating respirable particles of a pharmaceutical formulation (including both solid particles and liquid particles) containing the virus as an aerosol suspension, and then causing the subject to inhale the respirable particles. Methods and apparatus for administering respirable particles of pharmaceutical formulations are well known, and any conventional technique can be employed.

In another embodiment, the present invention relates to antibodies specific for the above-described virus. For instance, an antibody can be raised against any of the viral proteins or against a portion thereof. Persons with ordinary skill in the art using standard methodology can raise monoclonal and polyclonal antibodies to the a polypeptide of the present invention. Material and methods for producing antibodies are well known in the art (see for example Goding, in, *Monoclonal Antibodies: Principles and Practice*, Chapter 4, 1986). The antibodies can be used to monitor the presence or activity of alphaviruses and potentially for passive immunization and as a therapeutic to reduce symptoms of infection by VEE.

In a further embodiment, the present invention relates to a method of detecting the presence of VEE viral infection or antibodies against VEE virus in a sample. Using standard methodology well known in the art, a diagnostic assay can be constructed by coating on a surface (i.e. a solid support) for example, a microtitration plate or a membrane (e.g. nitrocellulose membrane), all or a unique portion of VEE virus described above, and contacting it with the serum of a person suspected of having a viral infection. The presence of a resulting complex formed between the VEE virus and antibodies specific therefor in the serum can be detected by any of the known methods common in the art, such as fluorescent antibody spectroscopy or colorimetry or microscopy. This method of detection can be used, for example, for the diagnosis of VEE viral infections.

In yet another embodiment, the present invention relates to a method of detecting the presence of VEE in a sample. Using standard methodology well known in the art, a diagnostic assay can be constructed by coating on a surface (i.e. a solid support) for example, a microtitration plate or a membrane (e.g. nitrocellulose membrane), antibodies specific for VEE, and contacting it with serum or tissue sample of a person suspected of having a VEE viral infection. The presence of a resulting complex formed between virus in the serum and antibodies specific therefor can be detected by any of the known methods common in the art, such as fluorescent antibody spectroscopy or colorimetry. This method of detection can be used, for example, for the diagnosis of VEE viral infection.

In another embodiment, the present invention relates to a diagnostic kit which contains VEE virus and ancillary reagents that are well known in the art and that are suitable for use in detecting the presence of antibodies to and VEE in serum or a tissue sample. Tissue samples contemplated can be birds, horses, monkey, human, or other mammals.

In yet a further embodiment, the present invention relates to DNA or nucleotide sequences for use in detecting the presence or absence of or VEE virus using the polymerase chain reaction (PCR). The DNA sequence of the present invention can be used to design primers which specifically bind to the viral RNA for the purpose of detecting the presence, absence, or quantitating the amount of virus. The primers can be any length ranging from 7–40 nucleotides, preferably 10–15 nucleotides, most preferably 18–25 nucleotides. Reagents and controls necessary for PCR reactions are well known in the art. The amplified products can then be analyzed for the presence or absence of viral sequences, for example by gel fractionation, with or without hyridization, by radiochemistry, and immunochemical techniques. Such a method can also be used to distinguish between vaccinated and infected animals, wherein a primer chosen to include a junction between the capsid gene and intervening sequences for example can detect only the rearranged 'vaccine' virus.

In yet another embodiment, the present invention relates to a diagnostic kit which contains PCR primers specific for rearranged VEE, and ancillary reagents that are well known in the art and that are suitable for use in detecting the presence or absence of rearranged VEE in a sample using PCR. Samples contemplated can be insects, animals, and human, such as mosquitoes, birds, poultry, equine, bovine, rodent, human, and other mammals.

In another embodiment, the present invention relates to a method of reducing VEE viral infection symptoms in a patient by administering to said patient an effective amount of anti rearranged VEE antibodies or antisera from a patient inoculated with the rearranged VEE. When providing a patient with anti-VEE antibodies, the dosage of administered agent will vary depending upon such factors as the patient's age, weight, height, sex, general medical condition, previous medical history, etc. In general, it is desirable to provide the recipient with a dosage of the above compounds which is in the range of from about 1 pg/kg to 10 mg/kg (body weight of patient), although a lower or higher dosage may be administered.

Having now described the invention, the following examples are provided to illustrate the present invention, and should not be construed as limiting thereof. In light of the present disclosure, numerous embodiments within the scope of the claims will be apparent to those of ordinary skill in the art.

The following examples are provided to illustrate the present invention, and should not be construed as limiting thereof.

The following materials and methods were used in the examples that follow.

Construction of the plasmid encoding the VEE glycoproteins in VEE replicon. The VEE replicon encoding the wild-type VEE glycoproteins was constructed by cloning the BamHI-HindIII rVEEGPpBBIII encoding the glycoprotein (Hodgson et al., 1999, *Vaccine* 17, 1151–60) downstream of the VEE 26S promoter in the KS replicon shuttle vector. The resulting plasmid was designated pKS-VGP. pKS-VGP was in turn digested with ApaI-NotI and the DNA fragment encoding the VEE glycoproteins under control of the 26S promoter was cloned into the VEE replicon (Pushko et al., 1997, *Virology* 239, 389–401). The resulting plasmid was designated VEE-REP-GP.

Generation of virus containing rearranged structural genes. A plasmid encoding the VEE capsid (Pushko et al., 1997, *Virology* 239, 389–401) and VEE-REP-GP were linearized with NotI and run-off transcription of capped RNA transcripts was carried out with T7 DNA-dependent, RNA polymerase. Cotransfection of both these transcripts into BHK-21 cells was carried out by electroporation. The BHK-21 cells were maintained in growth media for two days and the resulting supernatant analyzed by plaque assay on Vero cells. The virus generated from this experiment was designated RVE.

EXAMPLE 1

Analysis of the virulence RVE and its ability to be used as a vaccine was carried out by inoculation of 4 to 6 week old Balb/C mice. Groups of ten mice were inoculated with RVE diluted in media at doses of $10^3$, $10^5$ and $10^7$ pfu per animal and a control group of animals was inoculated with media containing no virus. At 21 days post-inoculation, all animals were healthy and showed no signs of VEE induced disease. This indicated that the RVE virions generated by in vivo recombination of the two transcipts were attenuated. The animals were challenged at 3 weeks after the initial inoculation with wild-type VEE at a dose of $10^4$ pfu per animal. The results of this experiment are shown in Table 1. All animals that received RVE were fully protected from challenge, whereas the control animals that were inoculated with only media died from exposure to wild-type VEE. Sera samples from surviving animals were collected at 20 days post-inoculation and 21 days post-challenge. Analysis of neutralizing antibody induced by RVE was completed using a standard plaque-reduction assay.

TABLE 1

| | Inoculation[a] | | Challenge[b] | |
|---|---|---|---|---|
| Dose of RVE (pfu) | Sick/Total | Dead/Total | Sick/Total | Dead/Total |
| $10^7$ | 0/10 | 0/10 | 0/10 | 0/10 |
| $10^5$ | 0/10 | 0/10 | 0/10 | 0/10 |
| $10^3$ | 0/10 | 0/10 | 0/10 | 0/10 |
| None* | 0/10 | 0/10 | 10/10 | 10/10 |

[a]inoculation subcutaneous with RVE
[b]challenge with VEE (TRD) at a dose of $10^4$ pfu/animal
*HBSS containing no virus at the time of inoculation

EXAMPLE 2

Neutralization Titer (PRNT) assay with VEE(Trd) as the target virus. ELISA analysis was conducted using live VEE(Trd) adsorbed to microtiter wells, and developed with a goat anti-mouse enzyme linked secondary antibody. The results of these serological assays are shown in Table 2 and Table 3.

TABLE 2

PRNT assay against VEE (TRD) generated by vaccination with RVE

| Dose | Prechallenge titer | Postchallenge titer |
|---|---|---|
| $10^3$ | 9352 | 11569 |
| $10^5$ | 10743 | 12341 |
| $10^7$ | 11314 | 15193 |

Titers given as geometric mean of ten animals

TABLE 3

ELISA of anti-VEE antibodies generated by vaccination with RVE

| Dose | Prechallenge titer | Postchallenge titer |
|---|---|---|
| $10^3$ | 58535 | 87677 |
| $10^5$ | 47771 | 100000 |
| $10^7$ | 58358 | 107341 |

Titers given as geometric mean of ten animals

EXAMPLE 3

Generation of Plasmids encoding RVE1.1 and RVE 4.4. Two separate plaque isolates of RVE generated from the transfection were selected and grown to high titer. RNA from each plaque isolate was purified and subjected to molecular analysis. Reverse transcription of the viral RNA was primed using oligo dT. Subsequent polymerase chain reaction (PCR) employing capsid and glycoprotein specific primers (in antisense and sense orientations, respectively) was used to generate the DNA encoding the regions between the glycoprotein and capsid region of RVE plaque isolates. This material was in turn cloned after digestion with SstII and NotI into VEE-REP-GP that had been digested with SstII and NotI. These clones were designated pRVE1.1 and pRVE4.4 and are depicted in FIG. 1.

EXAMPLE 4

Sequence analysis. Sequence analysis of the intervening regions between the glycoprotein encoding region and the 26S promoter of controlling capsid transcription was completed using RVE1.1 and RVE4.4 as template. The intervening sequences found in each plasmid are described as SEQ ID NO:1 for pRVE1.1 and SEQ ID NO:2 for pRVE4.4.

EXAMPLE 5

Generation of viruses from DRVE1.1 and pRVE4.4. The pRVE1.1 and pRVE4.4 plasmids were linearized by digestion with NotI and run-off transcription of capped RNA transcripts was carried out with T7 DNA-dependent, RNA polymerase. Transcripts were transfected into BHK-21 cells by electroporation. The BHK-21 cells were maintained in growth media for two days and the resulting supernatant analyzed by plaque assay on Vero cells. The virus generated by transfection of transcripts of pRVE1.1 and pRVE4.4 were designated RVE1.1.1 and RVE4.1.4, respectively.

Animal experiments with RVE1.1.1 and RVE4.1.4 are outlined below. RVE1.1.1 and RVE4.1.4 were used to inoculate of 4 to 6 week old Balb/C mice. Groups of ten mice were inoculated with each RVE diluted in media at doses of $10^3$, $10^5$ and $10^7$ pfu per animal and a control group of animals was inoculated with media containing no virus. At 28 days post-inoculation, all animals were healthy and showed no signs of VEE induced disease. This indicated that the RVE virions generated using the cloned plasmid material as starting material were fully attenuated. The animals were challenged at 4 weeks after the initial inoculation with wild-type VEE at a dose of $10^4$ pfu per animal. The results of this experiment are shown in Table 4. All animals that received RVE 4.1.4 were fully protected from challenge, whereas the control animals that were inoculated with only media died from exposure to wild-type VEE. All animals but one that received RVE1.1.1 were fully protected from challenge with wild-type VEE. The one animal that died exhibited a unilateral paralysis at three days post-challenge. Both the time of death and the symptoms prior to death of this animal are not typical of VEE induced disease in mice. These results indicate that virus derived from clone RVE1.1.1 and RVE4.1.4 are efficacious vaccines.

TABLE 4

Survival data from RVE 1.1.1 and RVE 4.1.4 inoculation followed by challenge with wild-type VEE (Trd).

| | Prechallenge | | Postchallenge | |
|---|---|---|---|---|
| | Sick/Total | Dead/Total | Sick/Total | Dead/Total |
| Dose RVE 1.1.1 | | | | |
| $10^3$ | 0/10 | 0/10 | 1/10 | 1/10 |
| $10^5$ | 0/10 | 0/10 | 0/10 | 0/10 |
| $10^7$ | 0/10 | 0/10 | 0/10 | 0/10 |
| Dose RVE 4.1.4 | | | | |
| $10^3$ | 0/10 | 0/10 | 0/10 | 0/10 |
| $10^5$ | 0/10 | 0/10 | 0/10 | 0/10 |
| $10^7$ | 0/10 | 0/10 | 0/10 | 0/10 |
| Media | | | | |
| | 0/10 | 0/10 | 10/10 | 10/10 |

EXAMPLE 6

Derivation of RVE from virulent V3000 Trinidad strain of VEE. Similarly to the original RVE viruses, the new rearranged VEE virus will be derived from the virulent V3000 Trinidad strain of VEE. This rearranged VEE virus will consist of the following V3000 elements (listed from 5' to 3'): 5' UTR-nonstructural proteins-26S promoter-glycoproteins-26S promoter-Capsid-3' UTR (UTR= untranslated region). This is similar to the original RVE constructs.

The difference between RVE variants and the new virus will be the following. The lengths of the intervening sequences will be minimal (shorter than in either RVE construct) and the nucleotide structure of the intervening sequences will be different that in either of the RVE constructs. The new rearranged VEE virus will be tested in mice similarly to the original RVE constructs. This will allow us to assess the role of specific intervening sequences (for example, additional 26S promoter) on attenuation.

What is claimed is:

1. An attenuated Venezuelan encephalitis virus (VEE) having a capsid gene and structural glycoproteins wherein the genome of said virus contains a rearrangement such that the structural glycoproteins precede the capsid gene.

2. The attenuated VEE of claim 1 wherein an intervening sequence is located between the glycoprotein genes and the capsid gene.

3. An immunogenic composition comprising an attenuated rearranged VEE according to claim 1.

4. A vaccine comprising an attenuated rearranged VEE according to claim 1.

* * * * *

UNITED STATES PATENT AND TRADEMARK OFFICE
CERTIFICATE OF CORRECTION

PATENT NO. : 6,296,854 B1
DATED : October 2, 2001
INVENTOR(S) : Pushko et al.

It is certified that error appears in the above-identified patent and that said Letters Patent is hereby corrected as shown below:

Title page,
Title, should read -- LIVE ATTENUATED VENEZUELAN EQUINE ENCEPHALITIS VACCINE --
The portion of the title "EQUIRE" should read -- EQUINE -- in both instances.

Signed and Sealed this

Ninth Day of April, 2002

Attest:

JAMES E. ROGAN
*Attesting Officer*     *Director of the United States Patent and Trademark Office*